United States Patent
Floan (10) Patent No.: US 10,099,155 B2
(45) Date of Patent: Oct. 16, 2018

(54) SCREEN FOR EXTRACTOR SYSTEM

(71) Applicant: Crown Iron Works Company, Roseville, MN (US)

(72) Inventor: Benjamin Wayne Floan, Andover, MN (US)

(73) Assignee: Crown Iron Works Company, Roseville, MN (US)

( * ) Notice: Subject to any disclaimer, the term of this patent is extended or adjusted under 35 U.S.C. 154(b) by 22 days.

(21) Appl. No.: 15/055,270

(22) Filed: Feb. 26, 2016

(65) Prior Publication Data

US 2017/0246556 A1    Aug. 31, 2017

(51) Int. Cl.
  *B01D 11/02*  (2006.01)
  *C07H 1/08*   (2006.01)
  *C11B 1/10*   (2006.01)

(52) U.S. Cl.
  CPC ............. *B01D 11/023* (2013.01); *C07H 1/08* (2013.01); *C11B 1/10* (2013.01)

(58) Field of Classification Search
  CPC ............ B01D 11/023; C11B 1/10; C07H 1/08
  See application file for complete search history.

(56) References Cited

U.S. PATENT DOCUMENTS

| | | | |
|---|---|---|---|
| 4,617,177 A | 10/1986 | Schumacher | |
| 4,751,060 A | 6/1988 | Kratochwill | |
| 5,407,631 A * | 4/1995 | Salisbury | B29B 11/06 264/128 |
| 5,591,416 A | 1/1997 | Kemper et al. | |
| 5,714,178 A | 2/1998 | Keener | |
| 5,770,082 A | 6/1998 | Anderson | |
| 2012/0074074 A1 | 3/2012 | Lean et al. | |
| 2013/0137812 A1 * | 5/2013 | Harvey | C08L 27/18 524/520 |
| 2014/0284205 A1 | 9/2014 | Medoff et al. | |
| 2015/0027858 A1 | 1/2015 | Brotzmann et al. | |
| 2015/0132198 A1 | 5/2015 | Floan et al. | |
| 2015/0336035 A1 | 11/2015 | Floan et al. | |
| 2015/0352470 A1 | 12/2015 | Danon | |
| 2017/0252671 A1 * | 9/2017 | White | C08C 1/04 |

FOREIGN PATENT DOCUMENTS

DE   4115615 A1 * 11/1992 .............. A21B 3/07
WO   2015126463 A2   8/2015

OTHER PUBLICATIONS

English translation of DE4115615 (Year: 1992).*
International Patent Application No. PCT/US2017/019313, International Search Report and Written Opinion dated May 23, 2017, 17 pages.
"Wedge Wire Screens & Tubes," Progress Industry Group, Nov. 2012, 8 pages.

* cited by examiner

*Primary Examiner* — Regina M Yoo
(74) *Attorney, Agent, or Firm* — Fredrikson & Byron, P.A.

(57) ABSTRACT

A screen for an extractor system can have a top surface that a solid material contacts during operation of the extractor, a bottom surface opposite the top surface, and a plurality of apertures extending from the top surface through the bottom surface. In one example, the bottom surface of the screen is coated with a non-stick coating while the top surface of the screen is devoid of the non-stick coating.

22 Claims, 4 Drawing Sheets

SCREEN FOR EXTRACTOR SYSTEM

TECHNICAL FIELD

This disclosure relates to solvent extractor systems and, more particularly, to screens for solvent extractor systems.

BACKGROUND

A variety of different industries use extractors to extract and recover substances entrained within solids. For example, producers of products from renewable organic sources use extractors to extract carbohydrates and/or oil from solid matter, such as soybeans, rapeseed, sunflower seed, peanuts, cottonseed, palm kernels, and corn germ. The matter is contacted with a solvent within the extractor, causing the desired product to be extracted from a surrounding cellular structure into the solvent. As another example, extractors are used to recover asphalt from shingles and other petroleum-based waste materials. Typically, the petroleum-based material is ground into small particles and then passed through an extractor to extract the asphalt from the solid material into a surrounding organic solvent.

Depending on the type of extractor used to perform extraction, the extractor can have one or more sections of screen along which material is moved during operation. For example, a percolation extractor may have a bed deck formed of a screen and a solvent distribution system positioned above the screen. In operation, feedstock material can travel along the bed deck from the inlet of the extractor toward the outlet of the extractor. As the feedstock moves along the bed deck, liquid solvent is discharged on top of the feedstock, causing the solvent to percolate through the feedstock and drain through the underlying screen. The solvent extracts different components from the feedstock as it percolates through the material.

In practice, the screens used in extractors can become plugged during the course of operation. Fine particulate from the feedstock being processed may agglomerate and reduce or completely block the pores of the underlying screen. As the porosity of the screen decreases over time, the extraction efficiency of the extractor may be reduced. To restore efficient operation, the operator of the extractor may be required to shut the extractor down, remove residual feedstock and solvent from the extractor, and manually clean the extractor screens. This can be a costly and time consuming process.

SUMMARY

In general, this disclosure is directed to screens for extractor systems. The screen may have a top surface that a solid feedstock material contacts during operation of the extractor, a bottom surface, and a plurality of pores arrayed across the screen structure and extending from the top surface through the bottom surface. In some examples, the screen includes a non-stick coating applied on the bottom surface of the screen but not on the top surface. As a result, the top surface of the screen is devoid of non-stick coating. The addition of the non-stick coating on the bottom surface of the screen may substantially reduce screen plugging and extend the amount of time the extractor can be used between cleanings even though the non-stick coating is not applied to the primary top surface of the screen the material contacts during operation.

Without wishing to be bound by any particular theory, it is believed that, in some applications, feedstock being processed on an extractor has a tendency to plug the extractor screens from the bottom surface upwards instead of the top surface downwards. The force of feedstock material traveling along and over the top surface of the screen may have a tendency to keep the pores open near the top surface of the screen while material may build up on the pores more readily near the bottom of the screen. As a result, coating the screen with a non-stick coating on the bottom surface but not on the top surface can have a disproportionally beneficial effect at reducing screen fouling and plugging.

Configuring an extractor screen with a non-stick coating on the bottom surface but not on the top surface can have a variety of real real-world benefits. In operation, feedstock material being processed may be conveyed along the top surface of the extractor screen, exposing the top surface to shear forces. Over extended service, a non-stick coating on the top surface of the screen may have a tendency to chip or flake away which, particularly for applications where material for human or animal consumption is being processed (e.g., soy protein concentrate), can contaminate the material. As another example, coating the top surface of the extractor screen with a non-stick coating can make the extractor hazardous for operators needing to walk on the screen during service. As yet another example, coating the top surface of the extractor screen with a non-stick coating can narrow the cross-sectional width of the screen where the screen interfaces with the feedstock material being processed, potentially reducing the efficiency of the extractor. For these and other reasons, configuring the extractor screen with a non-stick coating on the bottom surface but not on the top surface may meaningful improve the operational efficiency of the extractor while minimizing deleterious effects of the coating. That being said, in other applications according to the disclosure, an extractor screen may be configured with non-stick coating on both its top and bottom surface and/or on only its top surface. Such completely coated or top coated screens can be used to reduce plugging as compared to uncoated screens in appropriate applications.

While a screen according to the disclosure can be used in any desired applications, in some examples, the screen is implemented as a bed deck in an extractor. The bed deck may provide a surface (e.g., top surface of the screen devoid of non-stick coating) along which incoming material is deposited and transported through the extractor. For example, the extractor may be configured as a percolation extractor in which solid material is conveyed along different screens through different stages in which extraction fluid, or solvent, is distributed down over the solid material. A fluid distribution system can be positioned over the bed deck in each stage of the extractor and a fluid collection system positioned underneath the bed deck in each stage. In operation, the solid material can be conveyed along the screens and the liquid extraction fluid distributed over the fluid using the fluid distribution system in each stage. The extraction fluid can filter, or percolate, down through the solid material on the bed deck, extracting components from the solid material soluble in the fluid being used as an extraction fluid. The extraction fluid having an increased concentration of soluble compounds may drain through the screens and be collected by the fluid collection system.

In one example, an extractor is described that includes an extraction chamber, a screen configured to support a solid material as the solid material is conveyed through the extraction chamber, and a conveyance system configured to convey the solid material along the screen in a direction of material travel. The example specifies that the screen has a top surface that the solid material contacts during operation, a bottom surface opposite the top surface, and a plurality of apertures extending from the top surface through the bottom surface. In addition, the example specifies that the bottom surface of the screen is coated with a non-stick coating while the top surface of the screen is devoid of the non-stick coating.

The details of one or more examples are set forth in the accompanying drawings and the description below. Other features, objects, and advantages will be apparent from the description and drawings, and from the claims.

DETAILED DESCRIPTION

This disclosure is generally directed to screen configurations and extractor systems including such screen configurations. In some examples, a screen according to the disclosure is a structure having multiple apertures, or openings, extending through a thickness of the structure. The apertures can have a size large enough to be effective to allow extraction fluid to drain through the screen but small enough to keep solid material upon which an extraction process is being performed from falling through the apertures. For example, the size of the apertures may vary based on the size of the material being processed.

The apertures of the screen may be defined and bounded by sidewall surfaces that extend across the thickness, or depth, of the screen structure. For example, the sidewall surfaces may have a length equal to the thickness of the screen structure. In some configurations, the bottom surface of the screen and/or the sidewall surfaces of the apertures are coated with a non-stick coating. For example, the non-stick coating may be applied to the bottom surface of the screen structure, including the sidewall surfaces extending from the bottom surface toward the top surface of the screen structure. The top surface of the screen structure may or may not be further coated with the non-stick coating. As one example, the top surface of the screen structure may be masked (e.g., covered) while the bottom surface is coated with the non-stick coating, resulting in a screen structure where the bottom surface of the screen (optionally including the sidewall surfaces defining the apertures) are coated with the non-stick coating while the top surface is devoid of the non-stick coating.

While a screen according to the disclosure can be used in a number of different applications, including even independent of extractor systems, the screen may be particularly useful for use inside of an extractor. The screen can be positioned inside of the extractor such that solid material is conveyed along and over the top surface of the screen. For example, the screen can be used as a bed deck within an extraction chamber. Solid material can be conveyed along the bed deck and exposed to solvent to extract components of interest from the solid material. In some arrangements, the extractor may include a washing system configured to wash the screen, further reducing screen plugging and extending the operational window of the extractor between cleanings.

Figure 2:
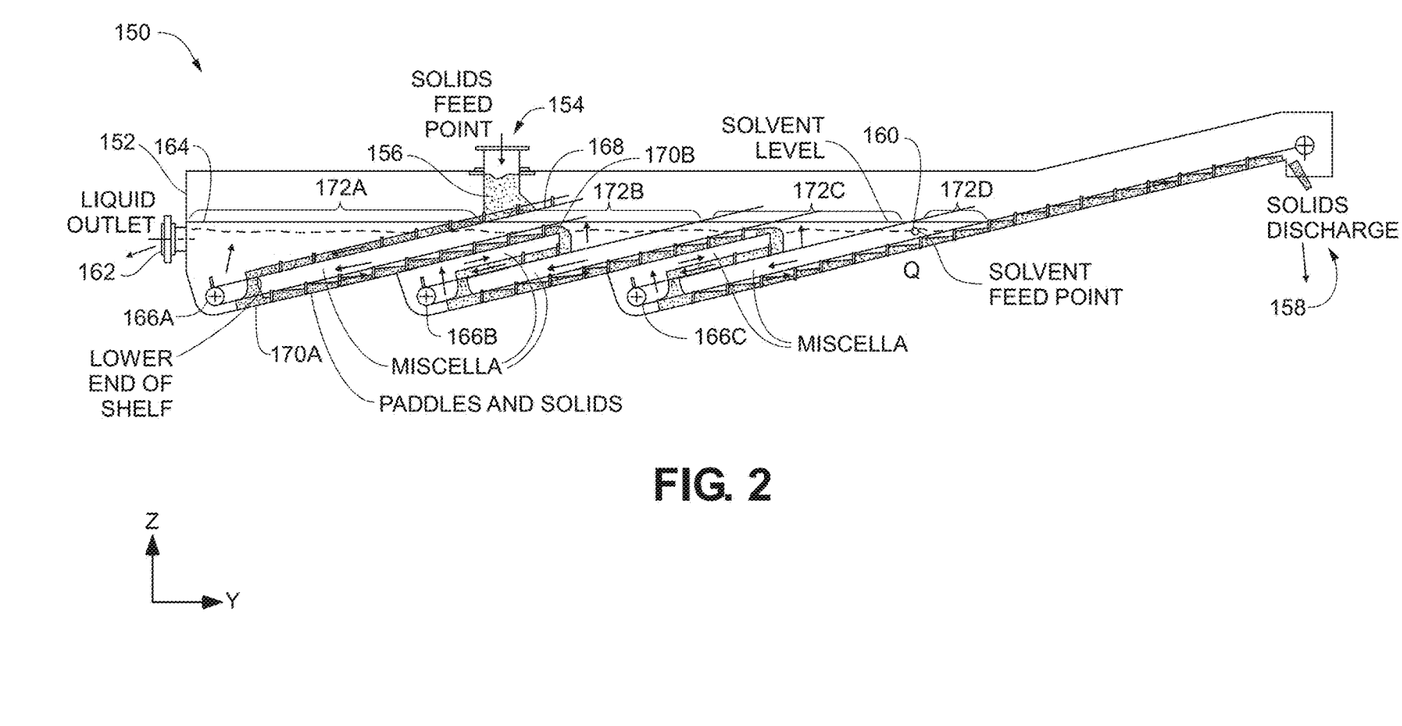
FIG. 2 is an illustration of another example configuration of an extractor that can utilize a screen according to the disclosure.
Figure 3A:
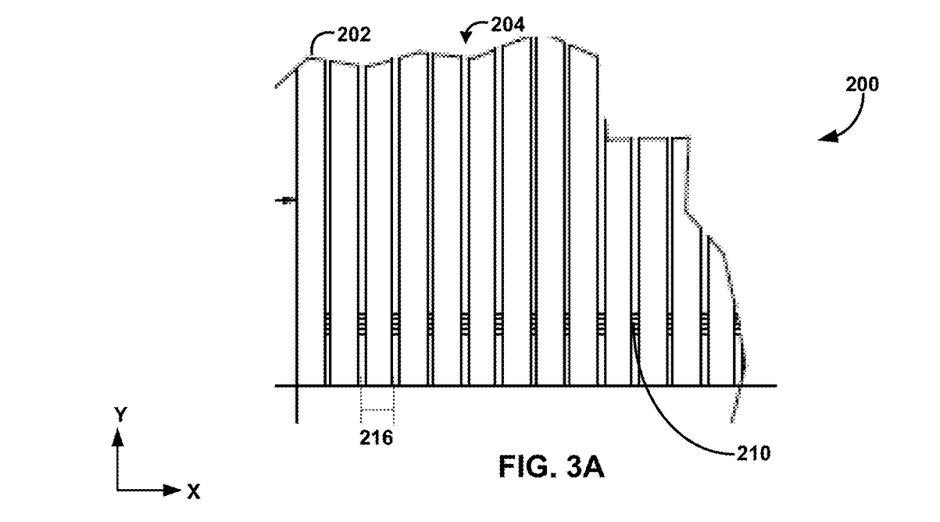
FIGS. 3A and 3B show a top view and a side view, respectively, of an example screen according to the disclosure.
Figure 3B:
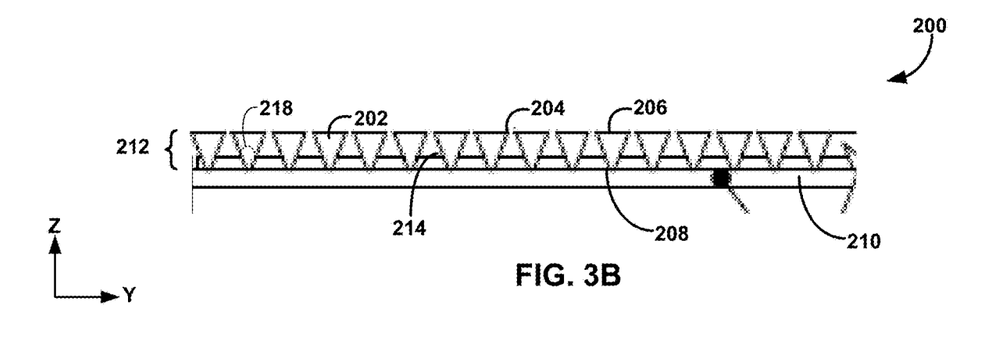

Details on example screen configurations according to the disclosure are described in greater detail with respect to FIGS. 3A and 3B. However, example extractor systems that can utilize a screen according to the disclosure are first described with respect to FIGS. 1 and 2.

Figure 1:
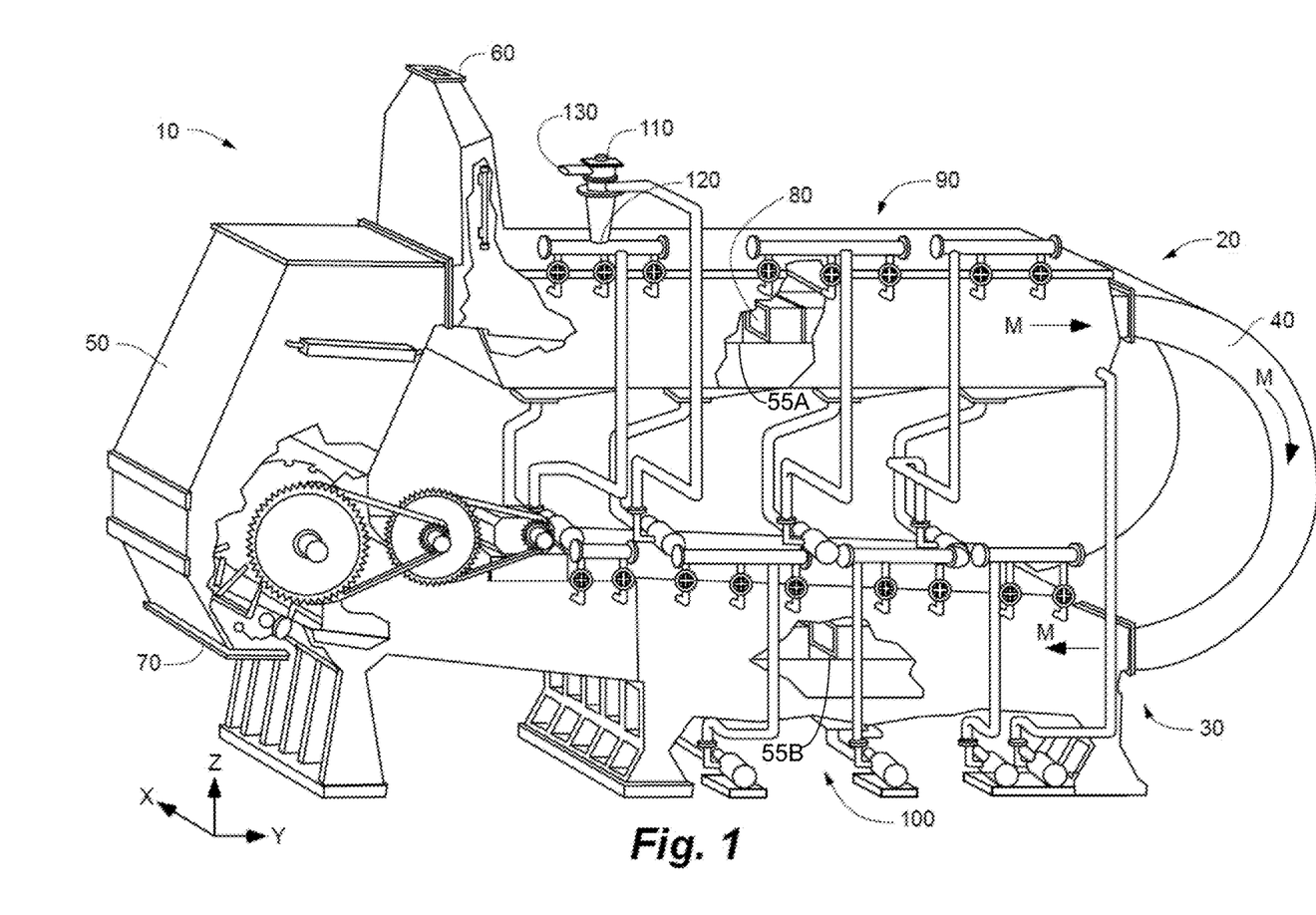
FIG. 1 is a perspective view of one example configuration of an extractor, shown with some parts broken away for purposes of illustration, that can utilize a screen according to the disclosure.

FIG. 1 is a perspective view of one example configuration of an extractor 10, shown with some parts broken away for purposes of illustration, that can utilize a screen according to the disclosure. In particular, extractor 10 is illustrated as a percolation extractor that includes a housing defining a passageway in the form of a loop disposed in a vertical plane. Extractor 10 includes upper and lower extraction sections 20, 30 each with a series of extraction chambers, a generally arcuate hollow transfer section 40 having its opposite upper and lower ends connected to first ends of the upper and lower extraction sections respectively, and a hollow, generally vertical return section 50 connected at its upper and lower ends respectively to the other ends of the upper and lower extraction sections. The upper extraction section can include an inlet portion 60 for delivery of solid material to the interior thereof in closely spaced relation to the upper end of the return section, and the lower end of the return section can define an opening 70 for discharge of the material after the product-of-interest has been extracted therefrom. The number of extraction chambers, or stages, provided by the extractor can vary depending on the desired size of the extractor. The extractor includes at least one extraction chamber, or stage, and typically includes multiple stages (e.g., 6 stages, 8 stages, or more). A Model III extractor commercially available from Crown Iron Works Company of Minneapolis, Minn., is a specific example of an extractor of this type.

In operation, solid material being processed is introduced into extractor 10 through inlet 60, processed within the extractor, and discharged through outlet 70. To support the solid material processed within extractor 10, the extractor can include a bed deck 55 that extends through one or more extraction stages. For example, when extractor 10 is configured as a continuous loop extractor as shown in FIG. 1, the extractor may have an upper bed deck 55A and a lower bed deck 55B (referred to collectively as "bed deck 55"). The upper bed deck 55A and lower bed deck 55B may form a continuous surface on top of which solid material being processed is conveyed through upper extraction section 20 and lower extraction section 30, respectively. For example, liquid extraction fluid dispensed on top of solid material being transported through extractor 10 may percolate through the thickness of a bed of the solid material before draining out through bed deck 55. As will be described, bed deck 55 can be implemented using a screen structure according to the disclosure.

To move solid material through extractor 10, the extractor can include a conveyance system. Extractor 10 in FIG. 1 includes a conveyance system 80, which can extend longitudinally through the looped passageway and be driven in a material flow direction "M" to move the material as a bed from the inlet portion 60 through the upper extraction section 20 toward and downwardly through the transfer section 40, and through the lower extraction section 30 toward the lower end of the return section and the discharge opening 70. In some configurations, the conveyor system includes a pair of laterally spaced endless link chains and a plurality of longitudinally spaced flights that extend transversely of the chains. A motor and gearing may be provided to drive the conveyor. For example, the conveyor may include flights that drag across the top surface of bed deck 55, causing solid material introduced through inlet 60 to convey across the top surface of the bed deck toward outlet 70.

In the example of FIG. 1, extractor 10 also includes a fluid supply system 90 disposed above the solid material and configured to apply a fluid to the solid materials in each extraction chamber. Extractor 10 also includes a fluid removal system 100 disposed below the solid material and configured for removing the fluid after it has passed through the solid materials in each extraction chamber. In some examples, the fluid supply system and the fluid removal system are in fluid communication via various recycle streams and the like. The fluid supply system may include a network of spray headers, pumps, and pipes to apply the fluid in each extraction chamber. The fluid supply system can apply (e.g., spray) the extraction fluid on top of the conveyed solid material, allowing the extraction fluid to then percolate through the material. The fluid removal system may include a network of drains, pumps, and pipes to collect the fluid after it has percolated through the solid material in each extraction chamber and deliver it to the fluid supply system of another extraction chamber or remove it from the system.

Extractor 10 can process any desired solid material using any suitable extraction fluid. Example types of solid material that can be processed using extractor 10 include, but are not limited to, oleaginous matter, such as soybeans (and/or soy protein concentrate), rapeseed, sunflower seed, peanuts, cottonseed, palm kernels, and corn germ; oil-bearing seeds and fruits; asphalt-containing materials (e.g., asphalt-containing roofing shingles that include an aggregate material such as crushed mineral rock, asphalt, and a fiber reinforcing); stimulants (e.g., nicotine, caffeine); alfalfa; almond hulls; anchovy meals; bark; coffee beans and/or grounds; carrots; chicken parts; chlorophyll; diatomic pellets; fish meal; hops; oats; pine needles; tar sands; vanilla; and wood chips and/or pulp. Fluids that can be used for extraction from solid material include, but are not limited to a hydrocarbon (e.g., acetone, hexane, toluene), alcohol (e.g., isopropyl alcohol, ethanol, other alcohols), and water.

Depending on the application, the operating temperature of the fluid and/or solid materials being processed inside of extractor 10 may be at an elevated temperature, such as a temperature greater than 25 degrees Celsius. For example, the temperature may range from 50 degrees Celsius and 100 degrees Celsius. Such elevated temperatures may have a tendency to breakdown certain materials being processed, such as organic materials, promoting blockage of the apertures formed in bed deck 55. That said, in other applications, the extractor may operate at ambient temperature (e.g., 15-25 degrees Celsius) or below ambient temperature.

In some examples, fluid having passed through the solid material is collected by a fluid removal system 100 and delivered to a cyclone-type separator 110 before it is removed from the extractor to separate any solid fines from the fluid before fluid discharge. The separator can have a lower discharge end 120 connected to an extraction chamber for re-delivery of separated solid materials in the extractor, generally in the first extraction chamber after the fresh solid material inlet 60. An outlet conduit 130 of the separator 110 delivers the fluid, generally a mixture of extraction fluid and soluble components extracted from the solid material into the extraction fluid (e.g., oil when processing oil seed) (commonly known as "miscella"), to other equipment, not shown, for separating the extraction fluid from the material extracted from the solid material being processed.

As solid material is conveyed through the extractor, spray headers from the fluid supply system 90 may spray recycled extraction fluid on the top of the material. The material can percolate through the material and through openings in bed deck 55, where it is collected in the network of drain pipes and may be delivered back to the network of spray headers for reapplication to the solid material in a different extraction chamber. To support the porous bed deck 55 inside of the extractor housing, a support frame may be provided under the bed deck that holds the bed deck in a fixed position during operation.

In the configuration shown, a delivery conduit connected to a source of liquid extraction fluid supply (not shown) is connected to the fluid supply system to supply fresh extraction fluid in at least one extraction chamber. In some embodiments, fresh extraction fluid is applied to the material in the last extraction chamber before the solid material discharge 70. For example, fresh extraction fluid may be applied to the material in the last extraction chamber before discharge 70 and, after being collected at the bottom of the chamber, recycled and applied on top of solid material in an adjacent upstream extraction chamber. By recycling collected extraction fluid from one extraction chamber to an adjacent upstream extraction chamber, liquid extraction fluid and solid material being processed can move in countercurrent directions through the extractor. For example, as extraction fluid is conveyed sequentially through adjacent extraction chambers between a fresh extraction fluid inlet adjacent discharge 70 and an enriched extraction fluid outlet adjacent inlet 60, the concentration of extract relative to extraction fluid may increase from a relatively small extract-to-extraction fluid ratio to a comparatively large extract-to-extraction fluid ratio. Similarly, as the solid material is conveyed in the opposing direction, the concentration of extract in the solid feedstock decreases from a comparatively high concentration at the inlet 60 to a comparatively low concentration at the outlet 70.

To help keep bed deck 55 clean and reduce clogging or complete blockage of the apertures in the bed deck, extractor 10 may include a wash system configured to wash the bed deck (e.g., intermittently, continuously) during operation. The wash system may include a conduct connected to a source of wash liquid and a plurality of nozzles positioned to direct washing liquid against bed deck 55. The washing system may spray a washing liquid that is the same (e.g., same composition) as the extraction fluid used to extract the solid material being processed. In different applications, the washing system may be positioned to spray washing liquid downwardly on a top surface of bed deck 55, or spray washing liquid upwardly on a bottom surface and underside of the bed deck, or both. Moreover, the nozzles of the washing system may or may not move (e.g., translate relative to bed deck 55), e.g., to increase the surface area of the bed deck washed. One example wash system that can be used is described in U.S. patent application Ser. No. 14/717,789, filed May 20, 2015, the entire contents of which are incorporated herein by reference.

As mentioned, a screen configuration according to the disclosure can be used in a variety of different applications, including different solid-liquid extractor designs than the configuration discussed with respect to FIG. 1. For example, FIG. 2 is an illustration of another example configuration of an extractor 150 that can utilize a screen according to the disclosure. In particular, extractor 150 is illustrated as an immersion extractor that includes a housing 152 containing one or more extraction stages through which a solid material being processed travels in a countercurrent direction with an extraction solvent. Housing 152 includes a feed inlet 154 configured to receive a continuous flow of solid material 156 being processed. Extractor 150 also includes a feed outlet 158 configured to discharge the solid material 156 after some or all of the extract has been extracted into solvent flowing through the extractor.

To provide a flow of solvent passing through extractor 150, housing 152 also includes a solvent inlet 160 that receives solvent devoid of extract or having a comparatively low concentration of extract. A solvent outlet 162 is provided on a generally opposite end of housing 152 to discharge solvent having passed through extractor 150. As solvent travels through housing 152 from inlet 160 to outlet 162, the solvent flows in a countercurrent direction from the flow of particulate material 156 passing through the extractor. The solvent intermixes with particulate material 156 within extractor 150, causing the extract carried by the solid material to transfer from the solid material to the solvent. Accordingly, in operation, solvent having a comparatively low concentration of extract enters at inlet 160 while solvent having an increased concentration of extract discharges at outlet 162. Likewise, fresh particulate solid material 156 carrying extract enters at inlet 154 while processed particulate material having a reduced concentration of extract is discharged at outlet 158.

Extractor 150 can be operated as an immersion extractor in which a pool or reservoir of solvent 164 is maintained in housing 152 to provide a desired solvent level inside the extractor. In such applications, solid material 156 is immersed (e.g., submerged) in the pool of solvent 164 as it moves through extractor 150. In some examples, solid material 156 remains completely submerged in the pool of solvent 162 as it travels through extractor 150, e.g., except when adjacent inlet 154 and outlet 156. In other examples, solid material 156 travels above the pool of solvent 164 at different stages in extractor 150 before falling off the end of a conveyor and dropping back into the pool of solvent. As one example, extractor 150 may be implemented using a Model IV extractor commercially available from Crown Iron Works Company of Minneapolis, Minn.

To contact particulate material 156 with solvent inside of extractor 150, the extractor has one or more conveyors that convey the material in a countercurrent direction through the pool of solvent 164. In the configuration of FIG. 2, for instance, extractor 150 has three conveyors 166A, 166B, 166C that convey particulate material 156 through the solvent pool 164 contained within housing 152. Solid material 156 can travel along decks or trays 168 positioned inside of extractor 150 to define a bed of material. Each bed deck 168 may define a receiving end 170A and a discharge end 170B. In operation, solid material 156 can drop onto the receiving end 170A of the bed deck 168 and then be conveyed along the bed deck by the conveyor until reaching the discharge end 170B. Upon reaching discharge end 170B, solid material 156 can drop off or fall over the terminal edge of the bed deck, for example, onto a lower bed deck.

In some examples, the pool of solvent 164 contained within housing 152 is divided into fluidly interconnected sub-pools, e.g., to provide different equilibrium extraction stages. For example, bed decks 168 may provide physical barriers that separate each sub-pool from each adjacent sub-pool and prevent solvent from flowing through the bed deck. In such examples, solvent may flow around the discharge end 170B of each bed deck rather than through the bed deck, allowing the solvent to flow in a countercurrent direction from solid material 156 through extractor 150.

In the example of FIG. 2, extractor 150 is illustrated as having four solvent pools 172A-172D. Each downwardly sloping bed deck 168 provides a barrier between adjacent pools with adjacent solvent pools being connected at the discharge end of a separating bed deck. In operation, each solvent pool of pools 172A-172D may have a different average extract-to-solvent concentration ratio to provide different stages of extraction. The concentration ratio may progressively increase from a lowest concentration adjacent solvent inlet 160 to a highest concentration adjacent solvent or outlet 162.

A screen according to the disclosure can be used in any suitable location within extractor 150. In some examples, the screen forms a portion of at least one of the decks 168 positioned inside of extractor 150. In such applications, solid material 156 can travel along the top surface of the screen as the material moves between inlet 154 and outlet 158.

Independent of the configuration of the extractor system with which a screen according to the disclosure may be used, the screen can have a variety of different structural configurations. In general, a screen may be any perforated structure that has multiple apertures (openings) delimited by bounding sections of material. The size, shape, and configuration of the openings may vary depending on the desired application of the screen. As one example, the screen may be formed by bonding (e.g., welding) intersecting and overlapping bars or wires into a lattice pattern. As another example, the screen may be formed by milling channels through the surface of a solid substrate to form the screen structure. As yet another example, the screen may be formed by punching or drilling openings into a solid substrate to form openings in the screen.

FIGS. 3A and 3B show a top view and a side view, respectively, of an example screen 200 that can be used according to the disclosure. While the following discussion is provided with respect to one example screen structure, it should be appreciated that the described features (e.g., shapes, dimensions, elements) may be implemented on screens formed using different techniques, as discussed above. As shown, screen 200 is formed of a plurality of closely spaced, parallel bars 202. A gap is formed between adjacent bars 202 thereby defining a plurality of apertures 204 that extend through the screen 200. Bars 202 have a top surface 206 and a bottom surface 208 opposite the top surface. In some examples, adjacent bars are joined together with one or more cross-bars or stiffeners 210 positioned underneath the bars 202. For example, bars 202 may be supported from underneath (e.g., in the Z-direction indicated on FIG. 1) with stiffeners 210. Stiffeners 210 may be perpendicular to the longitudinal axis of bars 202 or may be at a different angle relative to the longitudinal axis of the bars.

Each bar of bars 202 may be joined to stiffeners 210 to structurally support the bars and hold the bars in fixed position relative to each other. For example, each bar 202 may be welded to stiffener 210 along a portion of its bottom surface, e.g., causing stiffeners 210 to divide bars 202 into regions where bottom surface 208 is covered by stiffeners 210 and regions where bottom surface 208 is freely exposed. In alternative configurations, screen 200 may not have stiffeners 210. As discussed above, for example, apertures 204 may be milled or otherwise formed into a solid sheet of screen material, e.g., such that adjacent bars formed between milled channels are joined together at the side edges of the sheet of screen material.

In some configurations of screen 200, bars 202 are oriented such that their longitudinal axes are generally parallel with a direction of material travel "M" (e.g., such that length of the bars extends in the Y-direction indicated on FIG. 1 and the material also travels in the Y-direction indicated on FIG. 1). In other configurations, bars 202 are oriented such that their longitudinal axes are generally perpendicular with a direction of material travel "M" (e.g., such that length of the bars extends in the X-direction indicated on FIG. 1 and the material travels in the Y-direction indicated on FIG. 1). In either configuration, the top surface 206 of bars may be flat or planar (e.g., in the X-Y plane indicated on FIG. 1), providing a common horizontal plane (e.g., flat surface) on which solid material being processed can travel.

Independent of the specific configuration of a screen according to the disclosure, apertures of the screen may pass through the entire cross section of the screen structure, from the top surface of the screen through the bottom surface of the screen, to allow liquid to drain through the screen. In the configuration of FIG. 3B, apertures 204 extend from top surface 206 through bottom surface 208, providing a channel for liquid to flow from the top of the screen out through the bottom of the screen (e.g., except in regions blocked by stiffeners 210, when used). Apertures 204 have a depth 212 in the Z-direction indicated on FIG. 3B from the top surface 206 to the bottom surface 208. For example, the depth 212 of apertures 204 can define (at least in part) the thickness of screen 200 in the Z-direction, which is orthogonal to the direction of material flow "M" through extractor 10.

In the example of FIG. 3B, each bar of bars 202 has sidewalls 214 joining the top surface 206 to the bottom surface 208 and extending therebetween. The sidewalls 214 of adjacent bars bound and define an aperture between the bars. The depth 212 (or thickness) of bars 202 can vary depending on the mechanical strength needed for the particular application and the performance characteristics of screen 200. Further, the cross-sectional shape of bars 200 (e.g., in the Z-Y plane indicated on FIG. 3B) and, correspondingly the shape of apertures 204, can vary depending on the application.

In one configuration, the sidewalls 214 of bars 200 are perpendicularly oriented with respect to ground (e.g., by implementing bars 200 as rectangles) such that the cross-sectional area of aperture 204 at the top surface 206 (e.g., in the X-Y plane) is the same as the cross-sectional area of the aperture at the bottom surface 208. In other configurations, the sidewalls 214 of bars 200 are not perpendicularly oriented with respect to ground such that the cross-sectional area of aperture 204 at the top surface 206 is different than the cross-sectional area of the aperture at bottom surface 208.

In the example of FIG. 3B, bars 200 are illustrated as having a V-shape or triangular cross-sectional shape (e.g., in the Z-Y plane). As a result, the cross-sectional area of the bars decreases as the bars extend from top surface 206 to bottom surface 208. Conversely, the cross-sectional area of apertures 204 increases as apertures extend from the space formed between adjacent top surfaces 206 to adjacent bottom surfaces 208. A configuration where the cross-sectional area of the screen increases across the thickness of the screen (from top to bottom) can be useful to help minimize fouling or plugging. The cross-sectional area of the screen apertures can be made comparatively small near top surface 206, helping to prevent solid material positioned on and/or traveling along the top surface from dropping through apertures 204. The cross-sectional area of the screen apertures can be made comparatively large near bottom surface 208 such that, if material being processed tends to accumulate on the bottom side of the screen, there is additional open area to accommodate the collected material before flow-through efficiency of the screen starts to be impacted.

In general, the segments or cross-sectional members bounding apertures 204 can have any suitable cross-sectional shape (e.g., in the Z-Y plane). For example, they can have any polygonal (e.g., square, hexagonal) or arcuate (e.g., circular, elliptical) shape, or combinations of polygonal and arcuate shapes. In addition, while the specific dimensions of screen 200 can vary, in some examples, the distance between the edges of adjacent bars 202 (thereby setting the gap size of apertures 204 in the X-direction) ranges from 0.1 millimeters (mm) to 5 mm, such as from 0.5 mm to 2 mm, or from 0.1 mm to 2 mm. The distance 216 from the center of adjacent apertures 204 can vary and, in some examples, ranges from 1 mm to 50 cm, such as from 3 mm to 50 cm, or from 5 mm to 30 cm. In addition, the gap size of apertures 204 and/or spacing 216 between adjacent apertures may be constant across the length of the extractor in which the screen is installed or may vary.

For example, in some applications, different sections of screen may be installed in the extractor having different screen gap sizes and/or spacing between adjacent gaps. The open area of the screen may be smaller in areas of the extractor requiring less drainage and/or more liquid holdup. Conversely, the open area of the screen may be larger in areas of the extractor requiring greater liquid drainage and/or less liquid holdup. In some configurations, the open area of the screen is less than 50%, such as from 10% to 40%.

In applications where sidewalls 214 of bars 202 are angled (at a non-perpendicular angle) with respect to ground, the angle can vary depending on the intended application of the screen. In the example of FIG. 3B, the sidewalls of bars 200 are illustrated as being angled inwards at an internal angle 218. In some configurations according to the arrangement, the angle 218 ranges from 20 degrees to 70 degrees, such as from 30 degrees to 50 degrees.

In accordance with the present disclosure, a screen, such as a screen 200, is configured with a non-stick coating applied on at least a portion of the screen. The non-stick coating may be a material different than the material(s) used to fabricate the screen itself. The non-stick coating may reduce the coefficient of friction of the screen as compared to the coefficient of friction for the material used to fabricate the screen. As a result, the non-stick coating may help keep the apertures of the screen from filling and/or plugging, e.g., during operation of extractor 10.

In some examples, the non-stick coating is applied to at least bottom surface 208 of screen 200 but not top surface 206 of the screen. For example, the non-stick coating may be applied to bottom surface 208 and sidewalls 214 of bars 202 while the top surface 204 remains devoid of the non-stick coating. In configurations where screen 200 includes stiffeners 210, the non-stick coating may or may not also be applied to the stiffeners. In one example, the non-stick coating is applied to all surfaces of screen 200 except top surface 206. Alternatively, the non-stick coating may be applied to all surfaces of screen 200, including top surface 206. In such applications, the non-stick coating may or may not be subsequently removed from top surface 206 (e.g., by grinding or other mechanical or chemical removal techniques).

The specific type of non-stick coating used on screen 200 may vary, e.g., depending on the type of material intended to be processed using the screen and the operating conditions in which the screen will be used. In some examples, the non-stick coating is selected as one that reduces adhesion of organic material to the underlying material used to fabricate screen 200. For example, the non-stick coating may reduce adhesion of organic fines such as soy and/or canola fines, sugar molecules, and the like to screen 200. Such fines materials may have an average particle size less than 50 cm, such as less than 25 cm, or less than 10 cm.

One class of non-stick coatings that may be used is non-stick coatings that include a fluorocarbon molecule, such as fluoro-polymers. For example, the non-stick coating may be polytetrafluoroethylene, sold under the tradename Teflon®, or other suitable commercially-available fluorocarbon-rich coating. In some examples, the non-stick coating is applied to provide a dried coating thickness ranging from 0.01 mm to 2 mm, such as from 0.05 mm to 0.1 mm, although the thickness may vary depending on the type of material selected for the non-stick coating.

The screen itself may be formed of a variety of materials, which may be chosen based on the mechanical strength properties of the material. For example, the screen may be fabricated from metal (e.g., steel, stainless steel, titanium), ceramic, or other materials compatible with the intended process in which the screen is to be used. When the screen is only coated on the bottom-most surface and/or lower-facing sidewalls of the screen, the top surface of the screen may be devoid (e.g., entirely lacking) of non-stick coating.

Figure 4:
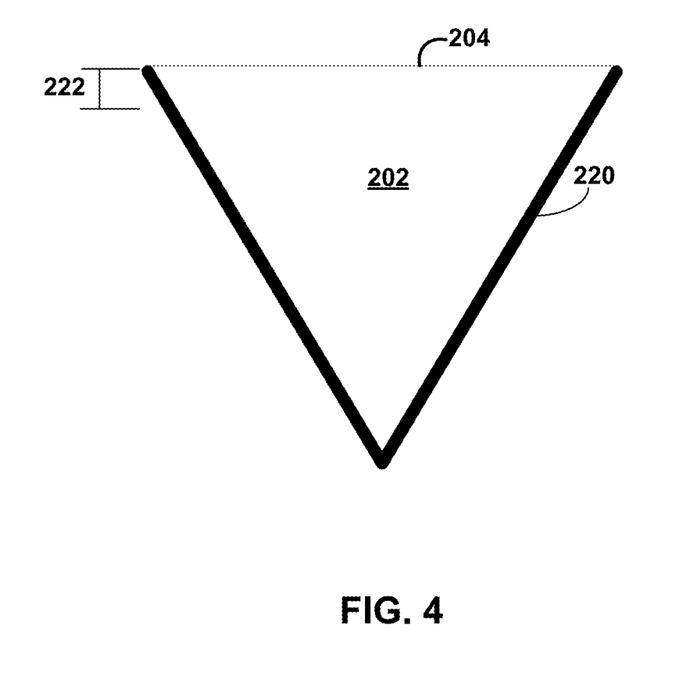
FIG. 4 is a side view of an example screen cross-sectional member showing an example a non-stick coating arrangement.

FIG. 4 is a side view of an example screen cross-sectional member 202 showing the bottom surface and sidewalls coated with a non-stick coating 220 while the top surface 204 is devoid of non-stick coating. In this example, the sidewalls are coated from where the edge of the top surface 204 intersects the edge of the sidewall down to the bottom-most surface. In some examples, the sidewalls are also devoid of non-stick coating a distance 222 from the top surface 204 down towards the bottom-most surface. While FIG. 4 illustrates distance 222 at one location for purposes of illustration such distance may vary, e.g., from 0.05 mm to 2 mm, such as 0.1 mm to 1 mm.

The non-stick coating can be applied to the material forming screen 200 using a variety of different coating techniques. For example, the non-stick coating may be applied by spray coating, roll coating, dip coating, powder coating, or other suitable technique, which may depend on the type of material selected for the non-stick coating. In some applications, top surface 206 is masked before applying the non-stick coating to the bottom surface 208 and/or sidewalls of the screen. Masking the top surface of the screen can help prevent coating overspray that can otherwise deposit on the top surface of the screen.

A screen carrying a non-stick coating according to the disclosure can be used to improve the service life and reduce the cleaning demands of the process equipment in which the screen is installed. While such a screen can be useful in an extractor arrangement as discussed above, the screen may be used in other applications in addition to or in lieu of an extractor. For example, the screen may be used as a deck in a desolventizer toaster positioned downstream of an extractor. The desolventizer toaster may receive solids material having undergone extraction and dry the solids material to remove residual solvent moisture.

Various examples have been described. These and other examples are within the scope of the following claims.

The invention claimed is:

1. An extractor comprising:
an extraction chamber;
a screen configured to support a solid material as the solid material is conveyed through the extraction chamber; and
a conveyance system configured to convey the solid material along the screen in a direction of material travel,
wherein the screen has a top surface that the solid material contacts during operation, a bottom surface opposite the top surface, and a plurality of apertures extending from the top surface through the bottom surface, the bottom surface of the screen being coated with a non-stick coating while the top surface of the screen is devoid of the non-stick coating.

2. The extractor of claim 1, wherein each of the plurality of apertures has a depth in a direction from the top surface to the bottom surface thereby forming aperture sidewalls, and the aperture sidewalls are coated with the non-stick coating.

3. The extractor of claim 1, wherein the non-stick coating comprises a coating configured to resist adhesion of sugar molecules and organic matter having an average size less than 10 centimeters.

4. The extractor of claim 1, wherein the non-stick coating comprises a fluorocarbon.

5. The extractor of claim 1, wherein the screen is fabricated from metal and the top surface is exposed metal.

6. The extractor of claim 1, wherein the non-stick coating has a thickness ranging from 0.01 millimeters (mm) to 0.1 mm.

7. The extractor of claim 1, wherein each of the plurality of apertures has a cross-sectional area, and the cross-sectional area increases as the aperture extends from the top surface to the bottom surface.

8. The extractor of claim 1, wherein each of the plurality of apertures has a depth in a direction from the top surface to the bottom surface and a width perpendicular to the depth and to the direction of material travel, the width of each of the plurality of apertures increasing as the aperture extends from the top surface to the bottom surface.

9. The extractor of claim 1, wherein the screen comprises a plurality of V-shaped bars attached to supports extending parallel to the direction of material travel.

10. The extractor of claim 1, wherein the screen comprises intersecting wires forming a grid.

11. The extractor of claim 1, wherein the conveyance system comprises at least one flight configured to move along the top surface of the screen in the direction of material travel, at least periodically causing a bottom surface of the at least one flight to scrape the top surface of the screen.

12. The extractor of claim 11, wherein the conveyance system comprises a plurality of flights extending generally perpendicularly from one or more endless drive lines positioned about the screen.

13. The extractor of claim 12, wherein the one or more endless drive lines comprise two drive lines positioned side-by-side.

14. The extractor of claim 1, further comprising a screen washing system configured to wash the screen.

15. The extractor of claim 14, wherein the screen washing system is disposed under the screen and supported against movement in the direction of material travel, the screen washing system including a washing fluid intake and a plurality of outlet nozzles directed upward towards the screen.

16. The extractor of claim 1, wherein the extractor chamber is configured to maintain a solvent pool in which solid material being processed is immersed during operation, and the screen is at least partially immersed in the solvent pool, thereby forming a bed deck of the extractor.

17. The extractor of claim 1, further comprising:
a fluid supply system disposed above the solid material and configured to apply a fluid to the solid material; and
a fluid removal system disposed below the solid material and configured for removing the fluid after it has passed through the solid material and the screen.

18. The extractor of claim 1, wherein the extractor is configured to operate at a temperature ranging from 50 degrees Celsius to 100 degrees Celsius.

19. The extractor of claim 1, wherein the screen comprises a plate having milled channels that define the plurality of apertures.

20. The extractor of claim 1, wherein each of the plurality of apertures has a gap size ranging from 0.1 millimeters to 2 millimeters.

21. The extractor of claim 1, wherein a spacing between adjacent apertures ranges from 3 mm to 50 cm.

22. The extractor of claim 21, wherein different regions of the screen have different spacing between adjacent apertures.

\* \* \* \* \*